United States Patent [19]

Matthews et al.

[11] Patent Number: 5,017,591

[45] Date of Patent: May 21, 1991

[54] THIAZOLYL METHYL)-2-2'-BI-1H-IMIDAZOLES AND USE AS HYPERTENSIVE AGENTS

[75] Inventors: Donald P. Matthews, West Chester, Ohio; Jeffrey P. Whitten, Zionsville, Ind.; James B. McCarthy, West Chester, Ohio

[73] Assignee: Merrell Dow Pharmaceuticals, Cincinnati, Ohio

[21] Appl. No.: 487,559

[22] Filed: Mar. 2, 1990

Related U.S. Application Data

[62] Division of Ser. No. 329,148, Mar. 27, 1989, Pat. No. 4,929,744, which is a division of Ser. No. 78,352, Jul. 28, 1987, Pat. No. 4,839,375.

[51] Int. Cl.$^5$ ............... A61K 31/415; A61K 31/38; C07D 277/20; C07D 277/32
[52] U.S. Cl. ............................ 514/369; 514/365; 548/182; 548/183; 548/202
[58] Field of Search ............... 548/202, 182, 183; 514/365, 369

[56] References Cited

U.S. PATENT DOCUMENTS 4,722,932  2/1988  Kawasaki et al. ............... 548/182

Primary Examiner—Anton H. Sutto
Assistant Examiner—J. Richter
Attorney, Agent, or Firm—William J. Stein

[57] ABSTRACT

This invention relates to novel (aryl or heteroaromatic methyl)-2,2'-1H-biimidazoles; to a process for their production comprising of reacting an appropriate alpha-brominated or alpha-chlorinated, substituted or nonsubstituted, methylated monoaromatic ring compound with 2,2'-bi-1H-imidazole in a solvent such as ethanol in the presence of a base such as sodium hydroxide under reflux conditions; and to pharmaceutical compositions and methods of treating hypertension with such compounds.

7 Claims, No Drawings

THIAZOLYL METHYL)-2-2'-BI-1H-IMIDAZOLES AND USE AS HYPERTENSIVE AGENTS

CROSS-REFERENCE TO RELATED APPLICATION

This is a divisional of application Ser. No. 329,148, filed Mar. 27, 1989, now U.S. Pat. No. 4,929,744 which is a divisional of application Ser. No. 078,352, filed July 28, 1987, now U.S. Pat. No. 4,839,375.

This invention relates to novel (aryl or heteroaromatic methyl)-2, 2'-bi-1H-imidazoles, to a process for their production, to pharmaceutical compositions of said compounds, and to methods of treating hypertension with such compounds.

More specifically, this invention relates to methylated 2, 2'-bi-1H-imidazoles of the general formula

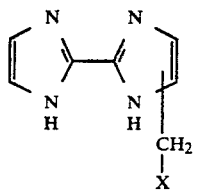

wherein X is 2- or 3-thienyl, 2- or 3-furyl, 2- or 4-thiazolyl or phenyl with each of said groups optionally being substituted; the optional substitution on said thienyl, furyl or thiazolyl groups being 1 or 2 moieties selected from the group consisting of chloro, fluoro, bromo and lower alkyl of from 1 to 6 carbon atoms; the optional substitution on said phenyl group being 1 or 2 moieties selected from the group consisting of chloro, bromo, fluoro, lower alkyl of from 1 to 6 carbon atoms, alkoxy of from 1 to 6 carbon atoms, trifluoromethyl, amino, sulfhydryl, and $S(O)_m R$ wherein m is 0, 1 or 2 and R is lower alkyl of from 1 to 6 carbon atoms;
the therapeutically acceptable acid addition salts thereof, and a process for preparing these compounds.

The compounds of this invention are dopamine β hydroxylase inhibitors, and as such are useful as antihypertensive agents. This invention also relates to a process for preparing imidazole compounds.

The term "$C_1$–$C_6$ lower alkyl" means a straight or branched-chain alkyl group containing from one to six carbon atoms, and includes methyl, ethyl, propyl, butyl, pentyl and hexyl groups. The term "$C_1$–$C_6$ alkoxy" refers to an —OR' group where R' is $C_1$–$C_6$ lower alkyl as above. When X is a mono-substituted group, the substituent can be located at any of the available positions on the aromatic or heteroaromatic ring. When X is a disubstituted group, the substituents can be the same or they can be different and they can be located at any of the available positions on the ring and oriented in any manner with respect to each other. Preferably, X is an unsubstituted group or is a monosubstituted group. Preferred substituents include chloro, fluoro and methoxy. The X—$CH_2$—moiety can be located at either the 1- or 4- position of the imidazole ring and both positions are encompassed by the present invention.

Illustrative examples of compounds of this invention include:
1-(3-thienylmethyl)-2, 2'-bi-1H-imidazole
4-[(4-methoxyphenyl)methyl]-2, 2'-bi-1H-imidazole
4-(3-thienylmethyl)-2, 2'-bi-1H-imidazole
1-(2-thienylmethyl)-2, 2'-bi-1H-imidazole
1-(2-furylmethyl)-2, 2'-bi-1H-imidazole
4-(3-furylmethyl)-2, 2'-bi-1H-imidazole
1-(2-thiazolylmethyl)-2, 2'-bi-1H-imidazole
4-(4-thiazolylmethyl)-2, 2'-bi-1H-imidazole
4-[(3–5-dichlorophenyl)methyl]-2, 2'-bi-1H-imidazole
1-(2,fluoro-5-thienylmethyl)-2, 2'-bi-1H-imidazole
4-(2-fluoro-4-thienylmethyl)-2, 2'-bi-1H-imidazole
4-(3-chloro-5-thienylmethyl)-2, 2'-bi-1H-imidazole
4-(3-chloro-5-furylmethyl)-2, 2'-bi-1H-imidazole
1-(2-methoxy-4-thienylmethyl)-2, 2'-bi-1H-imidazole
4-(2-methoxy-5-furylmethyl)-2, 2'-bi-1H-imidazole
4-(4-chloro-2-thiazolymethyl)-2, 2'-bi-1H-imidazole
and the therapeutically acceptable acid addition salts thereof.

Representative salts are those salts formed with non-toxic organic or inorganic acids, such as, for example, those formed from the following acids: hydrochloric, hydrobromic, sulfonic, sulfuric, phosphoric, nitric, maleic, fumaric, benzoic, ascorbic, succinic, methanesulfonic, acetic, propionic, tartaric, citric, lactic, malic, mandelic, cinnamic, palmitic, itaconic, benzenesulfonic and toluenesulfonic.

The biimidazoles of this invention can readily be prepared by the reaction depicted in reaction Scheme I:

REACTION SCHEME I

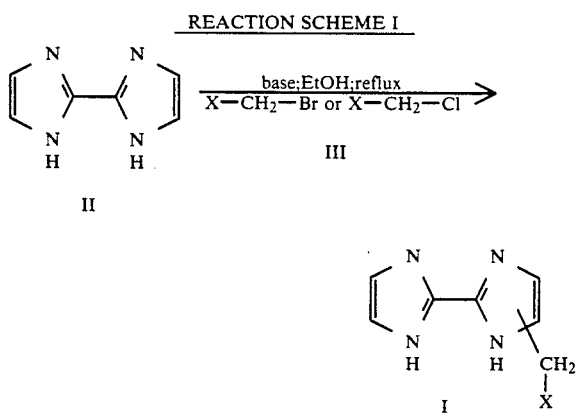

wherein X is as defined above.

In essence, Reaction Scheme I illustrates that the biimidazoles of formula I can be prepared by reacting the appropriate α- bromo or chloro compounds (III) with 2, 2'-bi-1H-imidazole (II) in a solvent such as ethanol (EtOH) and in the presence of a base such as sodium hydroxide (NaOH) under reflux conditions. The biimidazole starting material (II) can be obtained by a method of Matthews, D.P., Whitten, J.P., and McCarthy, J.R., set forth in *Synthesis*, 4,336, (1986).

When the desired product contains X as amino substituted phenyl, (III) would include the amino group protected by a silyl protecting group or protected as a phthalimide, and the resulting silylated compound or bi-imidazole-phthalimide would be appropriately deprotected to obtain the desired final product (I). Appropriate deprotecting agents for the silyl-protected compound would be, for example, ethanolic hydrochloric acid, or sodium fluoride. The phthalimide compound would be deprotected by means of hydrazine and alcohol.

Examples 1 through 5 are illustrations of Reaction Scheme I.

The process described above can also be used for the novel synthesis of known imidazole compounds wherein a readily available 2-substituted imidazole (IV) (wherein Y can be alkyl, aryl or trialkylsilyl, with the alkyl groups being straight- or branched-chain and containing up to ten carbon atoms, and the aryl groups being phenyl or naphthyl optionally substituted with groups such as alkyl of from 1 to 6 carbon atoms, halo, or alkoxy of from 1 to 6 carbon atoms) is reacted with the appropriate α- bromo or chloro compound (III), wherein X is as defined above, in a solvent such as ethanol (EtOH) in the presence of a base such as sodium hydroxide under reflux conditions to readily yield a mixture of 1- and 4- and 4, 5-bis- (X-methyl)-1H-imidazoles (V) which can be separated by flash chromatography. This reaction is depicted in Reaction Scheme II.

REACTION SCHEME II

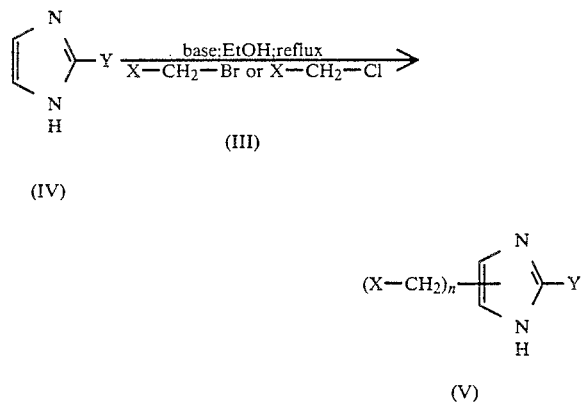

wherein X and Y are as defined above and n is 1 or 2

Example 6 is illustrative of Reaction Scheme II.

The following examples are present to illustrate the present invention, but they should not be construed as limiting it in any way.

EXAMPLE 1

4-[(4-Methoxyphenyl)methyl]-2, 2'-bi-1H-imidazole (1) and 1-[(4-Methoxyphenyl)methyl]-2, 2'-bi-1H-imidazole (2) 2, 2'-1H-Biimidazole was prepared by the method of Matthews, D.P., Whitten, J.P., and McCarthy, J.R., in *Synthesis*, 4,336 (1986). A mixture of 10 g (0.75 mol) biimidazole, 17 ml 5 N sodium hydroxide, and 150 ml ethanol was refluxed for one hour. After the mixture was cooled to room temperature, 8.6 g (0.055 mol) 4-methoxybenzyl chloride was added and the reaction was refluxed for 24 hours. The mixture was cooled to room temperature and was filtered to remove any unreacted 2, 2'-biimidazole solid. The filtrate was concentrated under reduced pressure to yield 14.7 g crude (1) and (2). Purification by flash chromatography (35% acetone/CH$_2$Cl$_2$ then 50% acetone) yielded 3.0 g (31%) (1) and 2.0 g (20%) (2).

(1): mp 204°-205° C. (isopropanol); $^1$H NMR (DMSO-d$_6$) 3.71 (s, 3), 3.95 (s, 2), 6.77-7.26 (m, 7); MS EI at 70eV 254(45) (M+), 147(100), 121(81). Anal. Calcd. for C$_{14}$H$_{14}$N$_4$O: C, 66.13; H, 5.55; N, 22.03. Found: C, 66.03; H, 5.65; N, 21.73.

(2): mp 138°-140° C. (toluene/hexane); $^1$H NMR (DMSO-d$_6$) 3.75 (s, 3), 5.85 (s, 2), 6.71-7.43 (m, 8); MS (EI at 70e V) m/z 254(6)(M+), 147(3), 121(100).

EXAMPLE 2

4-(Phenylmethyl)-2, 2'-bi-1H-imidazole (3) and 1-(Phenylmethyl)-2, 2'-bi-1H-imidazole (4)

The procedure described in Example 1 was followed, substituting benzyl bromide for the 4-methoxybenzyl chloride used in Example 1, to produce 16% (3), 23% (4) and 17% 1, 1' dialkylated biimidazole.

(3): mp 208°-210° C. (isopropanol); $^1$H NMR (DMSO-d$_6$) 3.94 (s, 2), 6.81-7.34 (m, 8); MS (EI at 70 eV) m/z 224 (30) (M+) 147(100), 91(33), 77(44). Anal. Calcd for C$_{13}$H$_{12}$N$_4$: C, 69.62; H, 5.39. Found: C, 69.67; H, 5.54.

(4): mp 138°-140° C. (toluene/hexane); $^1$H NMR (DMSO-d$_6$) 5.84 (s, 2), 6.99-7.28 (m, 9); MS (EI- at 70eV) m/z 224(13)(M+), 147(40), 91(100), 77(9). Anal. Calcd for C$_{13}$H$_{12}$N$_4$: C, 69.62; H, 5.39. Found C, 70.00; H, 5.49. The dibenzylated material had md 132°-134° C.; MS (EI at 70 eV) m/z 314(41)(M+), 237(23), 223(60), 91(100).

EXAMPLE 3

1-(2-Furylmethyl)-2, 2'-bi-1H-imidazole (5) and 4-(2-furylmethyl)-2, 2'-bi-1H-imidazole (6)

If the procedure of Example 1 is repeated using 2-bromomethylfuran rather than 4-methoxybenzyl chloride of Example 1, the products obtained are title compounds (5) and (6).

EXAMPLE 4

1-(2-Thiazolylmethyl)-2, 2'-bi-1H-imidazole (7) and 4-(2-Thiazolylylmethyl)-2, 2'-bi-1H-imidazole (8)

If the procedure of Example 1 is repeated using 2bromomethylthiazole rather than 4-methoxybenzyl chloride of Example 1, the products obtained are title compounds (7) and (8).

Similarly, if an appropriate halo- or methyl-substituted (brom omethyl) thiazole is used in the above procedure, the corresponding halo- or methyl-substituted thiazole product is obtained.

An alternate route for making a compound of this invention is presented in Example 5.

EXAMPLE 5

1-(2-Thienylmethyl)-2, 2'-bi-1H-imidazole (9)

Under nitrogen, a solution of 6.1 g (0.05 mol) 4-dimethylaminopyridine in 100 ml dimethylformamide was cooled to 10° C. and 5.3 g (0.05 mol) cyanogen bromide was added. The reaction was warmed to 20° C. and a precipitate of cyanogen bromide-dimethylaminopyridine complex formed. Upon cooling to 10° C., 3.3g (0.02 mol) 1-(2-thienyl-methyl)-1H-imidazole (which may be produced in a set forth in German patent application 3,228,266, July 19, 1982) was added. The reaction was stirred at room temperature for 6 hours and then quenched with 600 ml dilute sodium carbonate. The product was washed with water, dried (sodium sulfate) and concentrated under reduced pressure to yield 3.7 g crude 1-(2-thienylmethyl)-1H-imidazole-2-carbonitrile a was purified by flash chromatography (5% ethyl acetate/dichloromethane).

A mixture of 4.7 g (0.025 mol) a, 0.5 g sulfur, 20 ml methoxyethanol and 1.7 g (0.029 mol) ethylenediamine was stirred at room temperature under nitrogen for 15 minutes. The reaction was then heated and maintained at 120° C. for 6 hours, after which it was cooled to room temperature. After the addition, with stirring, of 300 ml water, 5.33 g (92%) off-white solid was collected and recrystallized (isopropanol) to yield 4',5'-dihydro-1-(2-thienylmethyl)-2, 2'-bi-1H-imidazole b (mp 101°–103° C.; Anal. Calcd for: N, 24.12; Found: N, 24.20).

A mixture of 3.0 g (0.0129 mol) of b, 7.2 g (0.083 mol) activated manganese oxide, and 200 ml dry dichloromethane was stirred at room temperature for 13 days. The reaction was filtered hot and the solids washed again with hot dichloromethane. Concentration under reduced pressure yielded 4.0 g crude (9). Purification by flash chromatography (ethyl acetate) resulted in 1.26 g (42%) of the title product (9). mp 153°–155° C.; Anal Calcd for $C_{11}H_{10}N_4S$: C, 57.37; H, 24.38; N, 24.33; Found: C, 57.25; H, 4.45; N, 24.30.

EXAMPLE 6

2-Phenyl-4-(3-thienylmethyl)-1H-imidazole (10), 2-Phenyl-4, 5-bis-(3-thienylmethyl)-1H-imidazole-(3-thienylmethyl)-1H-imidazole (11) and 2-phenyl-1-(12).

A mixture of 7.2 g (0.05 mol) 2-phenylimidazole, 12 ml 5M NaOH, and 100 ml ethanol was refluxed for 1 hour. After cooling to room temperature, 7.1 g (0.04 mol) 3-thienylmethyl bromide was added and the reaction was again heated to reflux. After 24 hours, the reaction was cooled and concentrated to give 23 g brown residue. The products were separated by flash chromatography (10% acetone/$CH_2Cl_2$ to yield 3.1 g (10), 2.6 g (11), 0.3 g (12) and also 3.0 g 2-phenylimidazole.

(10): mp 166°–168° C.; IR (KBr) 3100 cm-1 br; $^1$H NMR (DMSO-$d_6$) 3.90 (s, 2), 6.85–7.96 (m, 9), 12.37 (br s, 1); MS (EI at 70 eV) m/z 240(100)(M+), 157(9), 136(62), 97(8). Anal. Calcd for $C_{14}H_{12}N_2S$: C, 69.97; H, 5.03; N, 11.66. Found C, 69.83; H, 5.13; N, 11.58.

(11): mp 163–165° C.; IR (KBr) 3100 cm$^{-1}$ br; $^1$H NMR (DMSO-$d_6$) 3.88 (s, 4), 6.93–7.98 (m, 11), 12.20 (br s, 1); MS (EI at 70 eV) m/z 336 (87)M.+), 239(50), 97(100). Anal. Calcd for $C_{19}H_{16}N_2S_2$ C, 67.82; H, 4.79; N, 8.32. Found: C, 67.60; H, 4.85; N, 8.35.

(12): $^1$H NMR (DMSO-$d_6$) 5.42 (s, 2), 6.95–7.90 (m, 10); MS (EI at 70 eV) m/z 240(53)(M.+), 157(1), 136(2), 97(100).

The compounds of this invention inhibit the enzyme dopamine β-hydroxylase (DBH) and therefore are useful in the treatment of hypertension. An embodiment of this invention is a method of treating hypertension in a mammal which comprises administering to said mammal an effective antihypertensive amount of compound of formula I. Since DBH is a major enzyme in the synthetic pathway of norepinephrine (NE), the presence of an inhibitor should decrease the amount of NE produced, and thereby have an antihypertensive effect.

The DBH inhibitory properties of the compounds of this invention can readily be determined by standard and well-known procedures. For example, inhibition of DBH was determined by a procedure wherein enzymatic activity was ascertained in aqueous solution in the presence of molecular oxygen, an electron donor such as ascorbate, a substrate such as tyramine, an inhibitor, and the necessary cofactors for the enzyme at a pH of 4.5 to 5.5, preferably pH 5.0, and at a temperature of 20° C. to 40° C., preferably 37° C. The inhibitor was assayed over a range of concentrations. Each reaction was followed by measuring oxygen uptake as an indication of enzyme activity using a polarographic electrode and an oxygen monitor, following the method of S. May, et al., *J. Biol. Chem.*, 256, 2258 (1981). The DBH inhibitory activity of compounds of this invention is indicated in Table I.

TABLE I

| DBH INHIBITORY ACTIVITY | |
|---|---|
| Compound | $IC_{50}$* |
| 1-(3-thienylmethyl)-2,2'-bi-1H-imidazole | 29.0 μM +/− 6.0 μM |
| 4-(3-thienylmethyl)-2,2'-bi-1H-imidazole | 8.8 μM +/− 1.8 μM |
| 1-(2-thienylmethyl)-2,2'-bi-1H-imidazole | 65.5 μM +/− 4.3 μM |

*Concentration at which the reaction is inhibited by 50%.

Thus, based on this and other standard laboratory techniques used to evaluate DBH inhibitors, by standard toxicity tests and pharmacological assays for the determination of antihypertensive activity in mammals, and by comparison of these results with the results of known antihypertensive agents, the effective antihypertensive dosage of the compounds of this invention can readily be determined. In general, effective antihypertensive results can be achieved at a dose of about 5 to about 100 mg per kilogram body weight per day. Of course, the specific initial and continuing dosage regimen for each patient will vary according to the nature and severity of the hypertension as determined by the attending diagnostician.

In their function as therapeutically useful compounds, it is advantageous to administer the compounds to the host animal in admixture with an acceptable and suitable pharmaceutical carrier. Such preparations may be in such forms as, for example, tablets, caplets and suppositories, or in liquid forms, as for example, elixirs, emulsions, sprays and injectables. In the formulation of pharmaceutical preparations, such substances can be employed which do not react with active substances as, for example, water, gelatin, lactose, starches, magnesium sterate, talc, vegetable oils, benzyl alcohols, gums, polyalkylene glycols, petroleum jelly and the like.

What is claimed as new and useful is:

1. A compound of the general formula

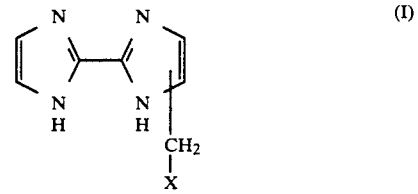

(I)

wherein X is the 2- or 4-thiazolyl groups optionally substituted with 1 or 2 moieties selected from the group consisting of chloro, fluoro, bromo and lower alkyl of from 1 to 6 carbon atoms.

2. A compound of claim 1 wherein the X—$CH_2$—moiety is located at the 1 position of the biimidazole.

3. A compound of claim 1 wherein the X—$CH_2$—moiety is located at the 4 position of the biimidazole.

4. A compound of claim 2 wherein X is substituted with chloro or fluoro.

5. A compound of claim 3 wherein X is substituted with chloro or fluoro.

6. A pharmaceutical composition comprising an effective amount of a compound of claim 1 and a pharmaceutically acceptable carrier.

7. A method of treating hypertension in a mammal which comprises administering to said mammal an effective amount of a compound of claim 1 or the therapeutically-acceptable salt thereof.

* * * * *